United States Patent
Kawamukai et al.

(10) Patent No.: US 10,736,323 B2
(45) Date of Patent: *Aug. 11, 2020

(54) ACIDIC OXIDANT-CONTAINING COMPOSITION HAVING ALUMINUM CORROSION-SUPPRESSING EFFECT AND USE THEREOF

(71) Applicant: Saraya Co., Ltd., Osaka-shi (JP)

(72) Inventors: Emiko Kawamukai, Kashiwara (JP); Satomi Sakai, Kashiwara (JP); Taro Furuta, Kashiwara (JP)

(73) Assignee: Saraya Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/042,657

(22) Filed: Sep. 30, 2013

(65) Prior Publication Data

US 2014/0030357 A1 Jan. 30, 2014

Related U.S. Application Data

(63) Continuation of application No. 13/201,419, filed as application No. PCT/JP2009/052861 on Feb. 19, 2009, now Pat. No. 8,574,632.

(51) Int. Cl.
*A01N 37/16* (2006.01)
*A01N 59/00* (2006.01)
*A61L 2/18* (2006.01)
*C23C 22/56* (2006.01)
*C23F 11/12* (2006.01)

(52) U.S. Cl.
CPC ............. *A01N 59/00* (2013.01); *A01N 37/16* (2013.01); *A61L 2/18* (2013.01); *C23C 22/56* (2013.01); *C23F 11/124* (2013.01)

(58) Field of Classification Search
None
See application file for complete search history.

(56) References Cited

U.S. PATENT DOCUMENTS

| 2,008,726 | A | 7/1935 | Reichert |
| 4,587,264 | A | 5/1986 | Jourdan-Laforte et al. |
| 5,077,008 | A | 12/1991 | Kralovic et al. |
| 5,545,343 | A | 8/1996 | Brougham et al. |
| 5,624,634 | A | 4/1997 | Brougham et al. |
| 5,696,046 | A | 12/1997 | Green |
| 5,900,256 | A | 5/1999 | Scoville, Jr. et al. |
| 6,472,358 | B1 | 10/2002 | Richter et al. |
| 6,627,657 | B1 | 9/2003 | Hilgren et al. |
| 2009/0074881 | A1 | 3/2009 | Kielbania, Jr. |

FOREIGN PATENT DOCUMENTS

| EP | 1 955 593 A2 | 8/2008 |
| JP | 58-157764 A | 9/1983 |
| JP | 07-502988 A | 3/1995 |
| JP | 2003-292996 A | 10/2003 |
| JP | 2005-187905 A | 7/2005 |
| JP | 2006-206535 A | 8/2006 |
| JP | 2007-254693 A | 10/2007 |
| JP | 2008-088062 A | 4/2008 |
| WO | WO 1993/007909 A1 | 4/1993 |
| WO | WO 2008/038744 A1 | 4/2008 |

OTHER PUBLICATIONS

U.S. Appl. No. 13/201,419, filed Aug. 12, 2011.
International Burau of WIPO, International Preliminary Report on Patentability in International Application No. PCT/JP2009/052861 (dated Aug. 23, 2011).
Japanese Patent Office, International Search Report in International Application No. PCT/JP2009/052861 (dated Mar. 31, 2009).
Japanese Patent Office, Office Action in Japanese Patent Application No. 2011-500394 (dated Feb. 15, 2011).

*Primary Examiner* — Jessica Worsham
(74) *Attorney, Agent, or Firm* — Leydig, Voit & Mayer, Ltd.

(57) ABSTRACT

The invention provides a liquid composition containing (a) an acidic oxidant, (b) nitric acid or a salt thereof, and (c) at least one carboxylic acid selected from the group consisting of monocarboxylic acids, dicarboxylic acids, and tricarboxylic acids, or a salt thereof. The liquid composition can be used to disinfect or sterilize a subject that includes a portion made of an aluminum-based metal.

19 Claims, No Drawings

ACIDIC OXIDANT-CONTAINING COMPOSITION HAVING ALUMINUM CORROSION-SUPPRESSING EFFECT AND USE THEREOF

CROSS-REFERENCE TO RELATED APPLICATIONS

This patent application is a continuation of copending U.S. patent application Ser. No. 13/201,419, filed Aug. 12, 2011, which is the U.S. national phase of International Patent Application No. PCT/JP2009/052861, filed on Feb. 19, 2009, which are incorporated by reference in their entireties herein.

TECHNICAL FIELD

The present invention relates to a liquid composition used mainly for sterilization or disinfection. In particular, the present invention relates to an acidic liquid composition having a sterilizing or disinfecting action, and an excellent aluminium corrosion-suppressing effect.

BACKGROUND ART

Since acidic oxidants have excellent sterilizing effects, they are widely used in the fields of medicine and foods as disinfectants and sterilizing agents. In particular, since acidic oxidants containing percarboxylic acids, such as peracetic acid, and hydrogen peroxide are capable of performing disinfection or sterilization in a short period of time, they are effective disinfecting/sterilizing agents for environments and apparatuses that cannot be physically disinfected.

Meanwhile, acidic oxidants have corrosiveness on metals and often deteriorate metal materials or cause rust, and thus often cause troubles for the function and appearance of such metals.

Among metals, in particular, with respect to aluminium or metals containing aluminium such as aluminium alloys (hereinafter also referred to as "aluminium-based metal"), corrosion tends to occur, such as occurrence of pitting corrosion in the presence of chloride ions, and precipitation of aluminium hydroxide due to hardness components in water. Such corrosion phenomena occur noticeably, especially in acidic conditions, in an accelerated manner.

In order to suppress corrosion of metals such as aluminium-based metals, corrosion suppressors have been used. For example, as corrosion suppressors, compositions containing chromates and molybdates are known. Such chromates and molybdates are used as rust preventatives in chemical sterilizing agents that disinfect or sterilize medical appliances that include metal portions, such as an endoscope in the medical field (see Patent Literature 1). However, such compositions are under control of the pollutant release and transfer register (PRTR) system, and are therefore impractical.

It is known that acid salts such as phosphates, nitrates, nitrites, molybdates, tungstates, borates, silicates, sulfates, sulfites and carboxylates, as well as chromates and molybdates, as well as; amine salts; and triazoles are effective as rust preventatives for metals (see Patent Literature 2). The carboxylates described in Patent Literature 2 are aliphatic-monocarboxylic-acid salts, for which the number of carbon atoms is 6 to 12; aliphatic-dicarboxylic-acid salts, for which the number of carbon atoms is 6 to 12; and aromatic-carboxylic-acid salts (paragraph [0016] of Patent Literature 2). Further, Patent Literature 3 describes that, among the above acid salts, nitrites and molybdates are used in combination for suppressing metal corrosiveness of acidic oxidants such as percarboxylic acids.

It is known that, among the various kinds of acid salts disclosed in Patent Literature 2, phosphates are rust preventatives having excellent corrosion-suppressing effects on aluminium-based metals. It is also known that a combined use of a phosphate and at least one compound selected from the group consisting of strontium compounds, magnesium compounds, and calcium compounds realizes an excellent corrosion-suppressing characteristic for aluminium-based metals at high temperatures, and a synergistic improvement of the cavitation damage-suppressing effect (Patent Literature 4).

CITATION LIST

Patent Literature

Patent Literature 1: U.S. Pat. No. 5,900,256
Patent Literature 2: Japanese Unexamined Patent Publication No. 2007-254693
Patent Literature 3: U.S. Pat. No. 5,077,008
Patent Literature 4: Japanese Unexamined Patent Publication No. 2005-187905

DISCLOSURE OF INVENTION

Technical Problem

Aluminium-based metals such as aluminium and aluminium alloys are often used in medical instruments, such as an endoscope, that require routine sterilization or disinfection treatment. Therefore, it is necessary to take measures against damaging the appearance and the function thereof by chemical disinfection or sterilization treatment.

Therefore, as mentioned above, various kinds of corrosion suppressors for aluminium-based metals have been developed, and adding such corrosion suppressors to chemical disinfectants or sterilizing agents to be used in combination has been proposed. However, in the fields of medicine and foods in particular, such corrosion suppressors must be safe for use, in consideration of residuals and toxicity. Further, in the case where acidic oxidants such as percarboxylic acids like peracetic acid and hydrogen peroxide are used as disinfectant or sterilizing agents, the stability of the acidic oxidants must also be considered.

Therefore, an object of the present invention is to provide an acidic liquid composition containing an acidic oxidant that has an excellent corrosion-suppressing characteristic (rust-preventing characteristic, tarnish-suppressing characteristic) for aluminium-based metals even under acidic conditions; that does not affect the appearance or function of such aluminium-based metals; and that can be effectively used for disinfection or sterilization of a subject that includes a portion made of aluminium-based metals, especially a medical instrument such as an endoscope.

Moreover, another object of the present invention is to provide a use of the acidic liquid composition as a disinfectant or sterilizing agent for a subject that includes a portion made of aluminium-based metals, and to provide a method for suppressing the aluminium corrosive action of the acidic oxidant.

Solution to Problem

The present inventors have studied diligently in order to solve the problem, and have found that by combining an acidic oxidant such as hydrogen peroxide and a percarboxylic acid, for example, peracetic acid, which are effective as disinfection or sterilizing agents, with (1) nitric acid and a salt thereof, and (2) a carboxylic acid (a mono-, di-tricarboxylic acid) and a salt thereof, the aluminium corrosive action of the acidic oxidant can be suppressed. The present inventors have also confirmed that a composition containing these three components can be effectively used as a disinfectant or a sterilizing agent for a medical instrument, such as an endoscope, that includes a portion made of aluminium-based metals such as aluminium and aluminium alloys.

The present invention has been completed based on the above findings, and includes the embodiments below.

(I) Acidic Liquid Composition (I-1) An acidic liquid composition containing (a) an acidic oxidant, (b) nitric acid or a salt thereof, and (c) at least one carboxylic acid selected from the group consisting of monocarboxylic acids, dicarboxylic acids, and tricarboxylic acids, or a salt thereof.

(I-2) The acidic liquid composition according to (I-1), wherein the (a) acidic oxidant is at least one selected from the group consisting of peracetic acid and hydrogen peroxide.

(I-3) The acidic liquid composition according to (I-2), which is prepared by blending peracetic acid at a proportion of 1 wt % or less, and preferably 0.05 to 1 wt %, or blending hydrogen peroxide at a proportion of 15 wt % or less, and preferably 3 to 15 wt %.

It should be noted that peracetic acid becomes an equilibrium mixture of acetic acid and hydrogen peroxide in water. Therefore, normally, peracetic acid does not exist in the same form as is in the acidic liquid composition (aqueous solution) described in (I-3). However, irrespective of the state of the acidic liquid composition, such an acidic liquid composition (aqueous solution) that is prepared by blending at least peracetic acid at the above proportion is included in the acidic liquid composition according to (I-3). In this sense, the above (I-3) can also be described as "the acidic liquid composition according to (I-2) containing the equilibrium mixture of acetic acid and hydrogen peroxide at a proportion of 1 wt % or less, and preferably 0.05 to 1 wt %; or hydrogen peroxide at a proportion of 15 wt % or less, and preferably 3 to 15 wt %".

(I-4) The acidic liquid composition according to (I-2), which is prepared by blending peracetic acid at a proportion of 1 wt % or less, and preferably 0.05 to 1 wt %, and blending hydrogen peroxide at a proportion of 2 wt % or less, and preferably 0.05 to 2 wt %.

As described above, such an acidic liquid composition (aqueous solution) that is prepared by blending at least peracetic acid in the above proportion is included, irrespective of the state thereof, in the acidic liquid composition according to (I-4). In this sense, the acidic liquid composition according to (I-4) can also be described as "the acidic liquid composition according to (I-2) containing an equilibrium mixture of acetic acid and hydrogen peroxide at a proportion of 1 wt % or less, and preferably 0.05 to 1 wt %; and hydrogen peroxide at a proportion of 2 wt % or less, and preferably 0.05 to 2 wt %".

(I-5) The acidic liquid composition according to any one of (I-1) to (I-4), wherein the (c) carboxylic acid is at least one selected from the group consisting of lactic acid, malic acid, succinic acid, and citric acid.

(I-6) The acidic liquid composition according to any one of (I-1) to (I-5), wherein the pH is less than 7, and preferably pH 1 to 6.

(I-7) The acidic liquid composition according to any one of (I-1) to (I-6), containing the (b) nitric acid or the salt thereof at a concentration of 0.1 to 10 wt %.

(I-8) The acidic liquid composition according to any one of (I-1) to (I-7), containing the (c) carboxylic acid or the salt thereof at a concentration of 0.1 to 30 wt %.

(I-9) The acidic liquid composition according to any one of (I-1) to (I-8), wherein the hardness is in a range of from 0 to 400 ppm in terms of calcium carbonate concentration, and in a range of from 0 to 280 ppm in terms of chlorine concentration.

(I-10) The acidic liquid composition according to any one of (I-1) to (I-9), further containing (d) an additive selected from the group consisting of chelating agents, stabilizing agents, preservatives, pH adjusters, and buffers.

(I-11) The acidic liquid composition according to any one of (I-1) to (I-10), which is a disinfectant or a sterilizing agent.

(I-12) The acidic liquid composition according to any one of (I-1) to (I-10), which is a disinfectant or a sterilizing agent for a subject containing, in part or in whole, aluminium or an aluminium alloy.

(II) Combination Product (II-1) A Combination Product Comprising:

(1) an acidic composition containing (a) an acidic oxidant contained in a container; and (2) a composition containing (b) nitric acid or a salt thereof, (c) at least one carboxylic acid selected from the group consisting of monocarboxylic acids, dicarboxylic acids, and tricarboxylic acids, or a salt thereof, and (d) an additive selected from the group consisting of chelating agents, stabilizing agents, preservatives, pH adjusters, and buffers, contained in a different container from the container of the (1) acidic composition.

(II-2) The combination product according to (II-1), wherein the (a) acidic oxidant in the (1) acidic composition is at least one selected from the group consisting of peracetic acid and hydrogen peroxide.

(II-3) The combination product according to (II-1) or (II-2), wherein the (c) carboxylic acid in the (2) composition is at least one selected from the group consisting of lactic acid, malic acid, succinic acid, and citric acid.

(II-4) The combination product according to (II-2) or (II-3), wherein either one of peracetic acid or hydrogen peroxide is used as the (a) acidic oxidant in the (1) acidic composition. As described above, peracetic acid becomes an equilibrium mixture of acetic acid and hydrogen peroxide in water. Therefore, in the case where peracetic acid is used as the acidic oxidant, the peracetic acid normally exists as the equilibrium mixture of acetic acid and hydrogen peroxide in the acidic composition. The (1) acidic composition according to (II-4) includes all acidic compositions, irrespective of the state thereof, that are prepared by blending at least peracetic acid.

(II-5) The combination product according to (II-2) or (II-3), wherein both of peracetic acid and hydrogen peroxide are used as the (a) acidic oxidant in the (1) acidic composition. In this case, peracetic acid exists as an equilibrium mixture of acetic acid and hydrogen peroxide in the acidic composition, and acetic acid and hydrogen peroxide are thus actually contained in the acidic composition. However, the (1) acidic composition according to (II-5) includes all acidic compositions, irrespective of the state thereof, that are prepared by blending at least peracetic acid and hydrogen peroxide.

(II-6) The combination product according to (II-4), wherein the (1) acidic composition contains the (a) acidic oxidant at a proportion of:
in the case where the acidic oxidant is peracetic acid, 15 wt % or less, and preferably 5 to 15 wt % (the final composition contains the equilibrium mixture generated from the peracetic acid, at a proportion of 15 wt % or less, and preferably 5 to 15 wt %); and in the case where the acidic oxidant is hydrogen peroxide, 30 wt % or less, and preferably 3 to 15 wt %.

(II-7) The combination product according to (II-4) or (II-6), wherein the (2) composition contains the (b) nitric acid or the salt thereof, and the (c) carboxylic acid or the salt thereof, at proportions of:
the (b) nitric acid or the salt thereof: 2 to 30 wt %; and
the (c) carboxylic acid or the salt thereof: 2 to 30 wt %.

(II-8) The combination product according to (II-4), (II-6) or (II-7), wherein the (1) acidic composition and the (2) composition are mixed before use such that the (a) acidic oxidant, the (b) nitric acid or the salt thereof, and the (c) carboxylic acid or the salt thereof are adjusted to be used at proportions of:
the (a) acidic oxidant:
in the case of peracetic acid: 1 wt % or less, and preferably 0.05 to 1 wt % (the final composition contains the equilibrium mixture generated from the peracetic acid, at a proportion of 1 wt % or less, and preferably 0.05 to 1 wt %); and in the case of hydrogen peroxide: 15 wt % or less, and preferably 3 to 15 wt %;
the (b) nitric acid or the salt thereof: 0.1 to 10 wt %; and
the (c) carboxylic acid or the salt thereof: 0.1 to 30 wt %.

(II-9) The combination product according to (II-8), wherein the (1) acidic composition and the (2) composition are mixed before use such that the pH is adjusted to be in a range of from 1 to 6, and the chelating agent is adjusted at a proportion of 0.01 to 0.5 wt %.

(II-10) The combination product according to (II-5), wherein the (1) acidic composition contains the (a) acidic oxidant at a proportion of:
peracetic acid: 15 wt % or less, and preferably 5 to 15 wt % (the final composition contains the equilibrium mixture generated from the peracetic acid, at a proportion of 15 wt % or less, and preferably 5 to 15 wt %); and
hydrogen peroxide: 30 wt % or less, and preferably 7 to 22 wt %.

(II-11) The combination product according to (II-5) or (II-10), wherein the (2) composition contains the (b) nitric acid or the salt thereof, and the (c) carboxylic acid or the salt thereof at proportions of:
the (b) nitric acid or the salt thereof: 2 to 30 wt %; and
the (c) carboxylic acid or the salt thereof: 2 to 30 wt %.

(II-12) The combination product according to (II-5), (II-10), or (II-11), wherein the (1) acidic composition and the (2) composition are mixed before use, such that the (a) acidic oxidant, the (b) nitric acid or the salt thereof, and the (c) carboxylic acid or the salt thereof are adjusted to be the following concentrations:
the (a) acidic oxidant:
peracetic acid at 1 wt % or less, and preferably 0.05 to 1 wt % (the final composition contains the equilibrium mixture generated from the peracetic acid, at a proportion of 1 wt % or less, and preferably 0.05 to 1 wt %), and hydrogen peroxide at 2 wt % or less, and preferably 0.05 to 1 wt %;
the (b) nitric acid or the salt thereof: 0.1 to 10 wt %; and
the (c) carboxylic acid or the salt thereof: 0.1 to 30 wt %.

(II-13) The combination product according to (II-12), wherein the (1) acidic composition and the (2) composition are mixed before use such that the pH is adjusted to be in a range of from 1 to 6, and the chelating agent is at a proportion of 0.01 to 0.5 wt %.

(II-14) The combination product according to any one of (II-1) to (II-13), which is a disinfectant or a sterilizing agent.

(II-15) The combination product according to any one of (II-1) to (II-13), which is a disinfectant or a sterilizing agent for a subject containing, in part or in whole, aluminium or an aluminium alloy.

(III) Preparation Method for Preparing Acidic Liquid Composition (III-1) A method for preparing an acidic liquid composition, the method comprising the step of mixing (a) an acidic oxidant, (b) nitric acid or a salt thereof, and (c) at least one carboxylic acid selected from the group consisting of monocarboxylic acids, dicarboxylic acids, and tricarboxylic acids, or a salt thereof.

(III-2) The method according to (III-1), wherein the (a) acidic oxidant is at least one selected from the group consisting of peracetic acid and hydrogen peroxide.

(III-3) The method according to (III-2), comprising the step of mixing the (a) acidic oxidant with the (b) nitric acid or the salt thereof, and the (c) carboxylic acid or the salt thereof, such that peracetic acid is at a concentration of 1 wt % or less, and preferably 0.05 to 1 wt % (the final composition contains an equilibrium mixture generated from the peracetic acid, at a proportion of 1 wt % or less, and preferably 0.05 to 1 wt %), or hydrogen peroxide is at a concentration of 15 wt % or less, and preferably 3 to 15 wt %.

(III-4) The method according to (III-2), comprising the step of mixing the (a) acidic oxidant with the (b) nitric acid or the salt thereof, and the (c) carboxylic acid or the salt thereof, such that the concentration of peracetic acid and hydrogen peroxide is 1 wt % or less, and preferably 0.05 to 1 wt % (the final composition contains an equilibrium mixture generated from the peracetic acid at a proportion of 1 wt % or less, and preferably 0.05 to 1 wt %), and the concentration of hydrogen peroxide is 2 wt % or less, and preferably 0.05 to 1 wt %.

(III-5) The preparation method according to any one of (III-1) to (III-4), wherein the (c) carboxylic acid is at least one selected from the group consisting of lactic acid, malic acid, succinic acid, and citric acid.

(III-6) The method according to any one of (III-1) to (III-5), wherein the pH of the acidic liquid composition is adjusted to be less than 7, and preferably pH 1 to 6.

(III-7) The method according to any one of (III-1) to (III-6), wherein the (b) nitric acid or the salt thereof is mixed such that the concentration thereof is 0.1 to 10 wt %.

(III-8) The method according to any one of (III-1) to (III-7), wherein the (c) carboxylic acid or the salt thereof is mixed such that the concentration thereof is 0.1 to 30 wt %.

(III-9) The method according to any one of (III-1) to (III-8), wherein the hardness of the acidic liquid composition is adjusted to be 0 to 400 ppm in terms of calcium carbonate concentration, and 0 to 280 ppm in terms of chlorine concentration.

(III-10) The method according to any one of (III-1) to (III-9), further comprising the step of mixing (d) an additive selected from the group consisting of chelating agents, stabilizing agents, preservatives, pH adjusters, and buffers.

(IV) Disinfection or Sterilization Method (IV-1) A disinfection or sterilization method comprising the step of:
treating a subject including an aluminium-based metal as a member using an acidic liquid composition containing (a) an acidic oxidant, (b) nitric acid or a salt thereof, and (c) at least one carboxylic acid selected from the group consisting of monocarboxylic acids, dicarboxylic acids, and tricarboxylic acids, or a salt thereof.

(IV-2) The method according to (IV-1), wherein the (a) acidic oxidant is at least one selected from the group consisting of peracetic acid and hydrogen peroxide.

(IV-3) The method according to (IV-2), wherein the acidic liquid composition that is used contains peracetic acid at a concentration of 1 wt % or less, and preferably 0.05 to 1 wt % (the final composition contains an equilibrium mixture generated from the peracetic acid, at a proportion of 1 wt % or less, and preferably 0.05 to 1 wt %), or hydrogen peroxide at a concentration of 15 wt % or less, and preferably 3 to 15 wt %.

(IV-4) The method according to (IV-2), wherein the acidic liquid composition that is used contains peracetic acid at a concentration of 1 wt % or less, and preferably 0.05 to 1 wt % (the final composition contains the equilibrium mixture generated from the peracetic acid at a proportion of 1 wt % or less, and preferably 0.05 to 1 wt %), and hydrogen peroxide at a concentration of 2 wt % or less, and preferably 0.05 to 2 wt %.

(IV-5) The method according to any one of (IV-1) to (IV-4), wherein the (c) carboxylic acid is at least one selected from the group consisting of lactic acid, malic acid, succinic acid, and citric acid.

(IV-6) The method according to any one of (IV-1) to (IV-5), wherein the pH of the acidic liquid composition is less than 7, and preferably pH 1 to 6.

(IV-7) The method according to any one of (IV-1) to (IV-6), wherein the acidic liquid composition is used that contains the (b) nitric acid or the salt thereof at a concentration of 0.1 to 10 wt %.

(IV-8) The method according to any one of (IV-1) to (IV-7), wherein the acidic liquid composition is used that contains the (c) carboxylic acid or the salt thereof at a concentration of 0.1 to 30 wt %.

(IV-9) The method according to any one of (IV-1) to (IV-7), wherein the acidic liquid composition is used whose hardness is in a range of from 0 to 400 ppm in terms of calcium carbonate concentration, and in a range of from 0 to 280 ppm in terms of chlorine concentration.

(IV-10) The method according to any one of (IV-1) to (IV-9), wherein the acidic liquid composition is used that contains (d) an additive selected from the group consisting of chelating agents, stabilizing agents, preservatives, pH adjusters, and buffers, in addition to the (a) acidic oxidant, the (b) nitric acid or the salt thereof, and the (c) carboxylic acid or the salt thereof.

(V) Method for Suppressing Corrosiveness on Aluminium (V-1) A method for suppressing corrosiveness of an acidic oxidant on aluminium, wherein
the (a) acidic oxidant is used in combination with (b) nitric acid or a salt thereof, and (c) at least one carboxylic acid selected from the group consisting of monocarboxylic acids, dicarboxylic acids, and tricarboxylic acids, or a salt thereof.

(V-2) The method according to (V-1), wherein the (a) acidic oxidant is at least one selected from the group consisting of peracetic acid and hydrogen peroxide.

(V-3) The method according to (V-1) or (V-2), wherein the (c) carboxylic acid is at least one selected from the group consisting of lactic acid, malic acid, succinic acid, and citric acid.

Advantageous Effects of Invention

The acidic liquid composition of the present invention contains, as active ingredients, acidic oxidants such as peracetic acid and hydrogen peroxide, which do not cause problems of residuals or toxicity. Therefore, the acidic liquid composition of the present invention can be used as a chemical disinfectant or sterilizing agent in the fields of medicine and foods. In particular, since the acidic liquid composition of the present invention has an excellent corrosion-suppressing action for metals, especially aluminium, the acidic liquid composition can be effectively used as a disinfectant or sterilizing agent for a subject (for example, a medical instrument such as an endoscope) that is made of or contains in part an aluminium-based metal such as aluminium or an aluminium alloy.

It should be noted that in the present invention, corrosion means that the appearance or a function of an aluminium-based metal such as aluminium or an aluminium alloy is damaged by a chemical action. Specifically, examples of corrosion include a phenomenon of an appearance change or an occurrence of rust on an aluminium-based metal, and a phenomenon in which a metal surface is ionized due to oxidation-reduction reaction, and peeled off from the surface.

DESCRIPTION OF EMBODIMENTS (I) Acidic Liquid Composition

An acidic liquid composition of the present invention contains (a) an acidic oxidant, (b) nitric acid or a salt thereof (hereinafter referred to as "nitric acid product") and (c) at least one carboxylic acid selected from the group consisting of monocarboxylic acids, dicarboxylic acids, and tricarboxylic acids, or a salt thereof (hereinafter referred to as "carboxylic acid product"). The composition has a disinfecting or sterilizing action based on a disinfecting or sterilizing action of the acidic oxidant. Also, by using the (a) acidic oxidant in combination with the (b) nitric acid product and the (c) carboxylic acid product, an aluminium corrosive action of the (a) acidic oxidant is suppressed. Accordingly, the composition can be effectively used for disinfection or sterilization of a subject made of or containing in part an aluminium-based metal such as aluminium or an aluminium alloy.

It should be noted that in the present invention, an "aluminium-based metal" is a collective term for a metal made of aluminium and a metal containing aluminium in part as metallic substance, that is, an aluminium alloy. An aluminium alloy is not limited to a particular aluminium alloy, and may be any aluminium alloys whose international aluminium alloy numbers are 1000 s (pure aluminum), 2000 s (Al—Cu-based alloy), 3000 s (Al—Mn-based alloy), 4000 s (Al—Si-based alloy), 5000 s (Al—Mg-based alloy), 6000 s (Al—Mg—Si-based alloy), and 7000 s (Al—Zn—Mg-based alloy, Al—Zn—Mg—Cu-based alloy).

Preferably, examples of the (a) acidic oxidant targeted by the present invention are peracetic acid and hydrogen peroxide. These can be used singularly, or in combination.

In the case where only peracetic acid is used as the acidic oxidant, examples of the proportion of peracetic acid to be blended in the acidic liquid composition of the present invention are 1 wt % or less, preferably 0.05 to 1 wt %, and more preferably 0.05 to 0.5 wt %, at use concentration. It should be noted that peracetic acid exists in a state of an equilibrium mixture of acetic acid and hydrogen peroxide in water. Therefore, the proportion of peracetic acid to be blended in the acidic liquid composition means the concentration of an equilibrium mixture (peracetic acid, acetic acid, hydrogen peroxide) generated from the peracetic acid, in a prepared final acidic liquid composition (aqueous solution).

In the case where only hydrogen peroxide is used as the acidic oxidant, examples of the content of hydrogen peroxide in the acidic liquid composition of the present invention are 15 wt % or less, preferably 3 to 15 wt %, and more preferably 3 to 7.5 wt %, at use concentration. The lower limit of the amount of each acidic oxidant contained in the acidic liquid composition is preferably a minimum amount that allows the acidic liquid composition to exhibit a disinfecting action. Examples of the lower limit of peracetic acid are 0.05 wt %, preferably 0.2 wt % (0.05 wt %, preferably 0.2 wt % as an equilibrium mixture generated from the peracetic acid), and more preferably 0.3 wt %. Examples of the lower limit of hydrogen peroxide are 3 wt %, preferably 4 wt %, and more preferably 5 wt %.

In the case where peracetic acid and hydrogen peroxide are used in combination as the acidic oxidant, examples of the proportion of peracetic acid to be blended in the acidic liquid composition of the present invention are 1 wt % or less, preferably 0.05 to 1 wt %, and more preferably 0.05 to 0.5 wt %, at use concentration (concentration as an equilibrium mixture generated from the peracetic acid). Examples of the content of hydrogen peroxide are 2 wt % or less, preferably 0.05 to 1 wt %, and more preferably 0.05 to 0.5 wt % at use concentration.

Examples of the (b) nitrate to be used in combination with the (a) acidic oxidant are an alkali metal salt of nitric acid, such as, preferably, sodium nitrate and potassium nitrate; and more preferably potassium nitrate. The nitric acid or the salt thereof is blended at a proportion such that the use concentration thereof in the acidic liquid composition of the present invention is 0.1 to 10 wt %. Preferably, the use concentration is 0.1 to 5 wt %, and more preferably 0.1 to 1 wt %.

Examples of the (c) carboxylic acid to be used in combination with the (a) acidic oxidant and (b) nitric acid or the salt thereof are a low-molecular-weight monocarboxylic acid, a low-molecular-weight dicarboxylic acid, and a low-molecular-weight tricarboxylic acid, each of which has a molecular weight of preferably 200 or less. Here, an example of preferable monocarboxylic acids is lactic acid (molecular weight 90.08); examples of preferable dicarboxylic acids are malic acid (molecular weight 134.09) and succinic acid (molecular weight 118.09); and an example of preferable tricarboxylic acids is citric acid (molecular weight 192.13). Among these carboxylic acids, lactic acid, malic acid, and citric acid are hydroxy acids. Examples of salts of these carboxylic acids are alkali metal salts of a carboxylic acid and sodium, and a carboxylic acid and potassium; and alkaline earth metal salts of a carboxylic acid and calcium, and a carboxylic acid and magnesium.

The (c) carboxylic acid and the salt thereof is used at a proportion such that the use concentration thereof in the acidic liquid composition of the present invention is 0.1 to 30 wt %. Preferably, the use concentration is 0.1 to 10 wt %, and more preferably 0.1 to 1 wt %.

The acidic liquid composition of the present invention is a liquid in which the above three components (a) to (c) are dissolved in a solvent. Preferably, an example of the solvent is water. In general, water with high hardness tends to accelerate corrosion of a metal. However, it has been observed that, as shown in EXAMPLES, the acidic liquid composition of the present invention has an excellent corrosion-suppressing action for an aluminium-based metal even when the acidic liquid composition is prepared using water having a relatively high hardness about 400 ppm in terms of calcium carbonate concentration, and 280 ppm in terms of chlorine concentration. Therefore, it can be considered that the acidic liquid composition of the present invention can fully exhibit a corrosion-suppressing action for an aluminium-based metal, if the hardness is at least in a range of from 0 to 400 ppm in terms of calcium carbonate concentration, and at least in a range of from 0 to 280 ppm in terms of chlorine concentration.

If a problem such as precipitation does not occur, (d) an additive selected from the group consisting of chelating agents, stabilizing agents, preservatives, pH adjusters, and buffers can further be blended in the acidic liquid composition of the present invention.

Here, the chelating agent is used for the purpose of chelating metals such as calcium and magnesium, copper(II) ion, iron(II) ion, iron(III) ion, and manganese ion in tap water. Specifically, examples of the chelating agent are ethylenediaminetetra acetate and a salt of hydroxyethane diphosphonic acid, and preferably tetrasodium of hydroxyethane diphosphonic acid. Such a chelating agent can be used at a proportion that can achieve the above objects. The chelating agent can be used at a use concentration of 0.01 to 1 wt %, and preferably 0.01 to 0.5 wt % in the 100 wt % acidic liquid composition, although not limited thereto.

The stabilizing agent is used for the purpose of stabilizing the disinfectant or sterilizing agent such as peracetic acid and hydrogen peroxide. Specifically, examples of the stabilizing agent are surfactants and solubilizing agents. Preferably, the stabilizing agent is propylene glycol or butylene glycol. Such a stabilizing agent can be used at a proportion that can attain the above objects. The stabilizing agent can be used such that the use concentration thereof in the acidic liquid composition (100 wt %) is 0.1 to 1 wt %, and preferably 0.2 to 0.3 wt %, although not limited thereto.

Examples of the preservative are benzoic acid or a salt thereof (for example, an alkali metal salt such as sodium benzoate), hexylene glycol, and the like. The preservative can be used such that the use concentration thereof in the acidic liquid composition (100 wt %) is 0.001 to 0.1 wt %, although not limited thereto.

The pH adjuster and the buffer are used in order to adjust the pH of the acidic liquid composition to be less than 7, preferably to be in a range of from pH 1 to 6, more preferably in a range of from pH 2 to 6, and further preferably in a range of from pH 3 to 5, and is not specifically limited to a specific value as long as the pH of the acidic liquid composition is in the above ranges. Specifically, examples of the pH adjuster are potassium hydroxide and sodium hydroxide, and examples of the buffer are phosphates. Preferably, the buffer is trisodium phosphate, or dipotassium phosphate.

The acidic liquid composition of the present invention can be prepared by mixing the (a) acidic oxidant, the (b) nitric acid or the salt thereof, and the (c) carboxylic acid or the salt thereof, as described above, and by adjusting, as necessary, the pH of the liquid composition by means of the buffer and the pH adjuster such that the pH is less than pH 7, preferably pH 1 to 6, more preferably pH 2 to 6, and further preferably pH 3 to 5. In the preparation step, in addition to the above-described components (a) to (c), the above-described (d) additive such as the above-described chelating agent and stabilizing agent may be blended as necessary.

The acidic liquid composition of the present invention prepared in this manner has an excellent disinfecting and sterilizing action against common bacteria, acid fast bacteria, fungi, viruses, and spores, based on the action of the (a) acidic oxidant. In particular, the acidic liquid composition of the present invention containing peracetic acid at a concentration of at least 0.05 wt %, preferably 0.2 wt %, and more preferably 0.3 wt % as the (a) acidic oxidant, has an excellent sterilizing action against common bacteria including gram-negative bacteria and gram-positive bacteria (*Staphylococcus aureus, Enterococcus faecium, Escherichia coli, Pseudomonas aeruginosa*), *Bacillus subtilis* spores (*Bacillus subtilis*), acid fast bacteria (*Mycobacterium terse*), and fungi (*Candida albicans*, or *Aspergillus* spp). In addition, the acidic liquid composition of the present invention has a corrosion-suppressing characteristic for aluminium-based metals such as aluminium and aluminium alloys.

Accordingly, the acidic liquid composition of the present invention can effectively disinfect or sterilize a subject of an aluminium-based metal or a subject containing an aluminium-based metal in part, while preventing corrosion such as rust or tarnish, and is thus especially useful as a disinfectant or sterilizing agent for such a subject. Preferably, an example of the subject made of an aluminium-based metal or the subject containing in part an aluminium-based metal is a medical instrument such as an endoscope, although not limited thereto.

As described above, the acidic liquid composition of the present invention includes ones containing the (a) acidic oxidant, the (b) nitric acid or the salt thereof, and the (c) carboxylic acid or the salt thereof in the following use concentrations. With respect to the (a) acidic oxidant, in the case of peracetic acid, peracetic acid: 1 wt % or less, and preferably 0.05 to 1 wt % (as the concentration of the equilibrium mixture generated from the peracetic acid); in the case of hydrogen peroxide, hydrogen peroxide: 15 wt % or less, and preferably 3 to 15 wt %; or in the case of peracetic acid and hydrogen peroxide used in combination, peracetic acid: 1 wt % or less, and preferably 0.05 to 1 wt % (as the concentration of the equilibrium mixture generated from the peracetic acid), and hydrogen peroxide: 2 wt % or less, and preferably 0.05 to 1 wt %; the (b) nitric acid or the salt thereof: 0.1 to 10 wt %; and the (c) carboxylic acid or the salt thereof 0.1 to 30 wt %. However, the acidic liquid composition is not limited thereto. The acidic liquid composition of the present invention may be a concentrate of the acidic liquid composition that is diluted before use to be in the above-described concentration ranges. The dilution rate is not limited in particular, but may be about 20 to 300 times.

Examples of the concentration of the (a) acidic oxidant, the (b) nitric acid or the salt thereof, and the (c) carboxylic acid or the salt thereof in the concentrate-type (diluted before use-type) acidic liquid composition include the following. With respect to the (a) acidic oxidant, in the case where peracetic acid is used singularly, peracetic acid: 15 wt % or less, and preferably 5 to 15 wt % (both in the concentration of the equilibrium mixture generated from the peracetic acid); in the case where hydrogen peroxide is used singularly, hydrogen peroxide: 30 wt % or less, and preferably 3 to 15 wt %; or in the case where peracetic acid and hydrogen peroxide are used in combination, peracetic acid: 15 wt % or less, and preferably 5 to 15 wt % (both in the concentration of the equilibrium mixture generated from the peracetic acid), and hydrogen peroxide: 30 wt % or less, and preferably 7 to 22 wt %; the (b) nitric acid or the salt thereof: 2 to 30 wt %; and the (c) carboxylic acid or the salt thereof: 2 to 30 wt %.

(II) Combination Product

As described above, the acidic liquid composition of the present invention may be one that contains in advance the (a) acidic oxidant, the (b) nitric acid or the salt thereof (nitric acid product), and the (c) carboxylic acid or the salt thereof (carboxylic acid product); and, in addition, the (d) at least one additive selected from the group consisting of chelating agents, stabilizing agents, preservatives, pH adjusters, and buffers. However, the present invention may be a combination product of (1) an acidic composition containing (a) an acidic oxidant, and (2) a composition containing (b) a nitric acid product, (c) a carboxylic acid product, and (d) at least one additive selected from the group consisting of chelating agents, stabilizing agents, preservatives, pH adjusters, and buffers, the (1) acidic composition and the (2) composition being contained in separate containers, respectively. An example of an aspect of the combination product is one commercially supplied to the market in the form of a two-part product or kit product that is composed of the (1) acidic composition and the (2) composition contained and packaged individually in separate containers; and a user thereof mixes them before use.

Here, for the acidic oxidant, the nitric acid or the salt thereof, the carboxylic acid or the salt thereof, the chelating agents, the stabilizing agents, the preservative, the pH adjusters, and the buffers, those described in (I) may be used.

The (1) acidic composition and the (2) composition contained and packaged individually in separate containers can be mixed before use, diluted with water as necessary, and thereby prepared as the acidic liquid composition described in the above (I); and thus can be used as a disinfectant or a sterilizing agent. The compositions (1) and (2) may be in the form of liquid, or may be in a solid state such as powder, granule, tablet, and the like.

The proportion of the (a) acidic oxidant in the (1) acidic composition, and the proportion of the (b) nitric acid product, the (c) carboxylic acid product, and the (d) additive component of the (2) composition are not limited to particular proportions; and may be any proportions that allow the acidic liquid composition of the present invention described in (I) to be prepared when the (1) and the (2) are mixed and further diluted before use with water or the like as necessary.

Specifically, in the case where the (1) acidic composition includes either one of peracetic acid and hydrogen peroxide as the (a) acidic oxidant, the combination product of the present invention may be any combination product that is prepared for use when the (1) acidic composition and the (2) composition are mixed before use and diluted as necessary, in the following manner. With respect to the (a) acidic oxidant, in the case of peracetic acid, peracetic acid: 1 wt % or less, preferably 0.05 to 1 wt %, and more preferably 0.05 to 0.5 wt % (the final composition contains an equilibrium mixture generated from the peracetic acid at a proportion of 1 wt % or less, preferably 0.05 to 1 wt %, and more preferably 0.05 to 0.5 wt %), or in the case of hydrogen peroxide, hydrogen peroxide: 15 wt % or less, preferably 3 to 15 wt %, and more preferably 3 to 7.5 wt %; the (b) nitric acid product: 0.1 to 10 wt %, preferably 0.1 to 5 wt %, and more preferably 0.1 to 1 wt %; and the (c) carboxylic acid product: 0.1 to 30 wt %, preferably 0.1 to 10 wt %, and more preferably 0.1 to 1 wt %. Further, preferably, with respect to the combination product, the (1) acidic composition and the (2) composition are mixed before use and diluted as necessary, such that the pH is adjusted in a range of from 1 to 6; and when a chelating agent is blended, the concentration thereof is adjusted to be 0.01 to 0.5 wt %.

Examples of the combination product are ones that contain: as the (1) acidic composition, peracetic acid at a proportion of 15 wt % or less, preferably 5 to 15 wt %, and more preferably 6 to 15 wt % (the final composition of (1) contains the equilibrium mixture generated from the peracetic acid at a proportion of 15 wt % or less, preferably 5 to 15 wt %, and more preferably 6 to 15 wt %); or hydrogen peroxide at a proportion of 30 wt % or less, preferably 3 to 15 wt %, and more preferably 7 to 15 wt %. Further, examples of the combination product are ones that contain: as the (2) composition, the (b) nitric acid product at a proportion of 2 to 30 wt %, preferably 2 to 20 wt %, and more preferably 2 to 10 wt %; and the (c) carboxylic acid product at a proportion of 2 to 30 wt %, preferably 2 to 20 wt %, and more preferably 2 to 10 wt %.

Further, as another aspect, in the case where the (1) acidic composition contains both of peracetic acid and hydrogen peroxide as the (a) acidic oxidant, the combination product of the present invention may be any combination product that is prepared for use in the following manner. The (1) acidic composition and the (2) composition are mixed before use and diluted as necessary, such that the concentration of the (a) peracetic acid is 1 wt % or less, preferably 0.05 to 1 wt %, and more preferably 0.05 to 0.5 wt % (the final composition contains the equilibrium mixture generated from the peracetic acid at a proportion of 1 wt % or less, preferably 0.05 to 1 wt %, more preferably 0.05 to 0.5 wt %); the concentration of hydrogen peroxide is 2 wt % or less, preferably 0.05 to 1 wt %, and more preferably 0.05 to 0.5 wt %; the concentration of the (b) nitric acid product is 0.1 to 10 wt %, preferably 0.1 to 5 wt %, and more preferably 0.1 to 1 wt %; and the concentration of the (c) carboxylic acid product is 0.1 to 30 wt %, preferably 0.1 to 10 wt %, and more preferably 0.1 to 1 wt %. Further, preferably, with respect to the combination product, the (1) acidic composition and the (2) composition are mixed before use and diluted as necessary, such that the pH is adjusted in a range of from 1 to 6; and when a chelating agent is blended, the concentration thereof is adjusted to be 0.01 to 0.5 wt %.

Examples of the combination product are ones that contain: as the (1) acidic composition, peracetic acid at a proportion of 15 wt % or less, preferably 5 to 15 wt %, and more preferably 6 to 15 wt %, (the (1) acidic composition contains the equilibrium mixture generated from the peracetic acid at a proportion of 15 wt % or less, preferably 5 to 15 wt %, and more preferably 6 to 15 wt %); and hydrogen peroxide at a proportion of 30 wt % or less, preferably 7 to 22 wt %, and more preferably 8 to 22 wt %. Further, examples of the combination product are ones that contain: as the (2) composition, the (b) nitric acid product at a proportion of 2 to 30 wt %, preferably 2 to 20 wt %, and more preferably 2 to 10 wt %; and the (c) carboxylic acid product at a proportion of 2 to 30 wt %, preferably 2 to 20 wt %, and more preferably 2 to 10 wt %.

(III) Disinfection Method

A disinfection method of the present invention can be performed by treating a subject by use of an acidic liquid composition having the (a) acidic oxidant, the (b) nitric acid or the salt thereof (nitric acid product), and the (c) carboxylic acid or the salt thereof (carboxylic acid product) described above. The acidic liquid composition may be one that further contains (d) at least one additive selected from the group consisting of chelating agents, stabilizing agents, preservatives, pH adjusters, and buffers, as necessary.

Examples of the concentration of the (a) acidic oxidant, the (b) nitric acid product, and the (c) carboxylic acid product in the acidic liquid composition to be used for the disinfection treatment of the subject include the following. With respect to the (a) acidic oxidant, in the case where peracetic acid is used singularly, peracetic acid: 0.05 to 1 wt %, and preferably 0.05 to 0.5 wt %, (an equilibrium mixture generated from the peracetic acid is contained at a proportion of 0.05 to 1 wt %, and preferably 0.05 to 0.5 wt %); in the case where hydrogen peroxide is used singularly, hydrogen peroxide: 3 to 15 wt %, and preferably 3 to 7.5 wt %; or in the case where peracetic acid and hydrogen peroxide are used in combination, peracetic acid: 0.05 to 1 wt %, and preferably 0.05 to 0.5 wt % (the equilibrium mixture generated from the peracetic acid is contained at a proportion of 0.05 to 1 wt %, and preferably 0.05 to 0.5 wt %), and hydrogen peroxide: 0.05 to 1 wt %, and preferably 0.05 to 0.5 wt %; the (b) nitric acid or the salt thereof 0.1 to 10 wt % (preferably 0.1 to 5 wt %); and the (c) carboxylic acid or the salt thereof 0.1 to 30 wt % (preferably 0.1 to 10 wt %).

In the case where a chelating agent is contained in the acidic liquid composition to be used in the disinfection treatment of the subject, examples of the content thereof are 0.01 to 1 wt %, and preferably 0.01 to 0.5 wt %. In the case where a stabilizing agent is contained in the acidic liquid composition, examples of the content thereof are 0.1 to 1 wt %, and preferably 0.2 to 0.3 wt %.

Preferably, since the above-described acidic liquid composition has an excellent aluminium corrosion-suppressing effect, an example of the subject to be treated is a subject that is made of or contains in part aluminium-based metals. Preferably, examples of such are medical instruments such as an endoscope.

Examples of the disinfection method include a method in which the subject is placed in contact with the acidic liquid composition of the present invention. Specifically, the examples include a method in which the subject is immersed in the acidic liquid composition of the present invention, a method in which the acidic liquid composition of the present invention is sprayed and applied onto the subject, a method in which the subject is caused to pass through the acidic liquid composition of the present invention, and a method in which the subject is wiped with a sheet or the like which is wet with the acidic liquid composition of the present invention.

(VI) Method for Suppressing Corrosiveness on Aluminium

The present invention provides a method for suppressing corrosiveness of an acidic oxidant such as peracetic acid or hydrogen peroxide on aluminium. The method can be performed using the (a) acidic oxidant in combination with the above-described (b) nitric acid or a salt thereof (nitric acid product) and the above-described (c) at least one carboxylic acid selected from the group consisting of monocarboxylic acids, dicarboxylic acids, and tricarboxylic acids, or a salt thereof (carboxylic acid product).

Examples of the concentration of the (a) acidic oxidant are as follows. In the case where peracetic acid is used singularly, peracetic acid: 1 wt % or less, preferably 0.05 to 1 wt %, and more preferably 0.05 to 0.5 wt % (an equilibrium mixture generated from the peracetic acid is contained at a proportion of 1 wt % or less, preferably 0.05 to 1 wt %, and more preferably 0.05 to 0.5 wt %); in the case where hydrogen peroxide is used singularly, hydrogen peroxide: 15 wt % or less, preferably 3 to 15 wt %, and more preferably 3 to 7.5 wt %. In the case where peracetic acid and hydrogen peroxide are used in combination, peracetic acid: 1 wt % or less, preferably 0.05 to 1 wt %, and more preferably 0.05 to 0.5 wt % (the equilibrium mixture generated from the peracetic acid is contained at a proportion of 1 wt % or less, preferably 0.05 to 1 wt %, and more preferably 0.05 to 0.5 wt %), and hydrogen peroxide: 2 wt % or less, preferably 0.05 to 1 wt %, and more preferably 0.05 to 0.5 wt %.

Examples of the proportion of the (b) nitric acid product to be used in combination with the (a) acidic oxidant at the concentrations described above are proportions that can achieve a concentration range of 0.1 to 10 wt % when the (b) nitric acid product and the (c) carboxylic acid product are used in combination with the (a) acidic oxidant. Preferably, examples of the proportion of the (b) nitric acid product are proportions that, when these are used in combination, achieve a concentration of the (b) nitric acid product of 0.1 to 5 wt %, and more preferably 0.1 to 1 wt %. Further, examples of the proportion of the (c) carboxylic acid product to be used in combination with the (a) acidic oxidant are proportions that, when the (b) nitric acid product and the (c) carboxylic acid product are used in combination with the (a) acidic oxidant, achieve a concentration range of from 0.1 to 30 wt %. Preferably, examples of such proportions are proportions that, when used in combination, achieve a concentration of the (c) carboxylic acid product of 0.1 to 10 wt %, and more preferably 0.1 to 1 wt %.

In this manner, the corrosiveness on aluminium of acidic oxidants such as peracetic acid and hydrogen peroxide can be suppressed; and, as a result, a disinfectant or sterilizing agent containing the acidic oxidant as an active ingredient can be applied for disinfection or sterilization of a subject that is made of or contains in part aluminium-based metals, such as a medical instrument such as an endoscope.

EXAMPLES

The present invention will be described in further detail with reference to the Experimental Examples below. It should be noted that the Experimental Examples below are merely examples for facilitating the description of the present invention, and are not intended to limit, in any way, the scope of the present invention.

It should be noted that, in the Experimental Examples below, when the acidic-oxidant-containing composition (aqueous solution) was prepared, artificial hard water whose hardness was 400 ppm in terms of calcium carbonate concentration and 280 ppm in terms of chlorine concentration was used in order to accelerate corrosion. In the Experimental Examples below, peracetic acid used in the preparation of the test liquid exists as an equilibrium mixture of acetic acid and hydrogen peroxide in the acidic-oxidant-containing composition (aqueous solution). Therefore, the concentration (w/w %) of peracetic acid shown in Tables 2, 4, 12, 14, 15, 16 and 18 in the Experimental Examples below means the concentration (w/w %) of the equilibrium mixture generated from the peracetic acid in the acidic-oxidant-containing composition (aqueous solution).

Experimental Example 1

(1) Subject

Test pieces (1.1 mm thickness×15 mm diameter, round shape) made of 5000-series aluminium alloys (A5052, A5056) and a 6000-series aluminium alloy (A6061) were used as subjects (subjects 1 to 3). The metal compositions of these aluminium alloys are shown in Table 1.

TABLE 1

|  | Si | Fe | Cu | Mn | Mg | Cr | Zn | Bi | Pb | Ti |
|---|---|---|---|---|---|---|---|---|---|---|
| A5052 | 0.25≥ | 0.40≥ | 0.10≥ | 0.10≥ | 2.2-2.8 | 0.15-0.35 | 0.10≥ | — | — | — |
| A5056 | 0.30≥ | 0.40≥ | 0.10≥ | 0.05-0.20 | 4.5-5.6 | 0.05-0.20 | 0.10≥ | — | — | — |
| A6061 | 0.40-0.8 | 0.7≥ | 0.15-0.40 | 0.15≥ | 0.8-1.2 | 0.04-0.14 | 0.25≥ | 0.40-0.70 | 0.40-0.70 | 0.15≥ |

(2) Acidic-Oxidant-Containing Aqueous Solution

Peracetic acid was used as the acidic oxidant. Acidic-oxidant-containing aqueous solutions (Test Liquids 1 to 15) containing potassium nitrate and citric acid at proportions listed in Table 2 in addition to the peracetic acid 0.3 w/w % were prepared using the above-described artificial hard water. Test Liquids 2 to 15 were adjusted to have the respective pHs shown in Table 2 using the pH adjuster (see Table 2).

TABLE 2

| Test liquid | Peracetic acid (w/w %) | Potassium nitrate (w/w %) | Citric acid (w/w %) | pH | pH adjuster |
|---|---|---|---|---|---|
| 1 | 0.3 | 0 | 0 | 2.7 | NONE |
| 2 | 0.3 | 0 | 0 | 3.5 | KOH |
| 3 | 0.3 | 0 | 0 | 4.0 | KOH |
| 4 | 0.3 | 0 | 0.8 | 3.5 | KOH |
| 5 | 0.3 | 0 | 1.2 | 3.5 | KOH |
| 6 | 0.3 | 0.1 | 0 | 3.5 | KOH |
| 7 | 0.3 | 0.1 | 0.8 | 3.5 | KOH |
| 8 | 0.3 | 0.1 | 1.2 | 3.5 | KOH |
| 9 | 0.3 | 0.2 | 0 | 3.5 | KOH |
| 10 | 0.3 | 0.2 | 0.8 | 3.5 | KOH |
| 11 | 0.3 | 0.2 | 1.2 | 3.5 | KOH |
| 12 | 0.3 | 0.4 | 0 | 3.5 | KOH |
| 13 | 0.3 | 0.4 | 0.8 | 3.5 | KOH |
| 14 | 0.3 | 0.4 | 1.2 | 3.5 | KOH |
| 15 | 0.3 | 10 | 30 | 3.5 | KOH |

(3) Corrosiveness Test

The above three subjects 1 to 3 (test pieces A5052, A5056, and A6061) were immersed in the above acidic-oxidant-containing aqueous solutions (Test Liquids 1 to 15) (room temperature: 20 to 25° C.). After seven days (after 1 week), these test pieces were withdrawn, and the degree of corrosion was observed from the appearance change and weight loss percentage (%).

(3-1) Appearance Change

The appearance of each subject was observed by viewing, and the appearance change was evaluated using the criteria below.

⊚: no rust or tarnish is observed.

○: the proportion of rust or tarnish is less than 10% over the entire surface area (100%) of the subject.

Δ: the proportion of rust or tarnish is 10 to 50% over the entire surface area (100%) of the subject.

▲: the proportion of rust or tarnish is greater than 50% over the entire surface area (100%) of the subject.

x: rust or tarnish is obviously observed over the entire surface area of the subject.

(3-2) Weight Loss Percentage (%)

The weight of each subject was measured before and after the immersion, and the weight loss percentage (%) was calculated using the formula below.

$$\text{weight loss percentage (\%)} = \frac{\left(\begin{array}{c}\text{weight of subject before immersion}-\\ \text{weight of subject after immersion}\end{array}\right)}{\text{weight of subject before immersion}} \times 100 \quad \text{[Formula 1]}$$

Table 3 shows the degree of corrosion (appearance change and weight loss percentage (%)) of the subjects after being immersed in the test liquids.

TABLE 3

| Test liquid | Subject 1 Test piece A5052 | | Subject 2 Test piece A5056 | | Subject 3 Test piece A6061 | |
|---|---|---|---|---|---|---|
| | Weight loss percentage | Appearance change | Weight loss percentage | Appearance change | Weight loss percentage | Appearance change |
| 1 | 3.58% | X | 4.34% | X | 4.26% | X |
| 2 | 2.10% | X | 3.38% | X | 3.29% | X |
| 3 | 1.90% | X | 3.07% | X | 2.72% | X |
| 4 | 2.69% | X | 3.54% | X | 3.89% | ▲ |
| 5 | 2.97% | X | 3.42% | X | 3.43% | ▲ |
| 6 | 0.13% | ▲ | 0.07% | ▲ | 2.50% | ▲ |
| 7 | 0.09% | Δ | 0.30% | Δ | 3.28% | Δ |
| 8 | 0.08% | ○ | 0.10% | ○ | 2.93% | ○ |
| 9 | 0.03% | X | −0.03% | X | 0.03% | X |
| 10 | 0.07% | ⊚ | 0.12% | ⊚ | 0.07% | ⊚ |
| 11 | 0.06% | ⊚ | 0.10% | ⊚ | 0.12% | ⊚ |
| 12 | 0.03% | X | −0.05% | X | −0.06% | X |
| 13 | 0.05% | ⊚ | 0.10% | ⊚ | 0.05% | ⊚ |
| 14 | 0.05% | ⊚ | 0.08% | ⊚ | 0.02% | ⊚ |
| 15 | −0.02% | ⊚ | 0.00% | ⊚ | 0.00% | ⊚ |

As seen from the above results, the following was revealed. When both of the nitrate and citric acid were blended in addition to peracetic acid (Test Liquids 7 to 8, 10 to 11, and 13 to 15), corrosion of the subject (appearance change (occurrence of rust, tarnish), weight loss) was significantly suppressed compared with the case where neither the nitrate nor citric acid was blended with peracetic acid (Test Liquids 1 to 3), the case where only the nitrate was blended and citric acid was not blended (Test Liquids 6, 9, 12), and the case where only citric acid was blended and the nitrate was not blended (Test Liquids 4 to 5).

Specifically, in the case where neither the nitrate nor citric acid was blended with peracetic acid (Test Liquids 1 to 3), obvious rust or tarnish was observed over the entire surface area of each subject. Moreover, the weight loss percentage tended to increase as the pH was lowered. Additionally, in the cases where citric acid was blended into Test Liquid 2 (Test Liquids 4 to 5), a corrosion-suppressing effect was not observed. In the case where the nitrate was blended in addition to peracetic acid (Test Liquids 4 to 5, 6, 9, 12), a tendency of weight loss suppression was observed. However, rust or tarnish was observed over 50 to 100% of the entire surface area of each subject, and a good corrosion-suppressing effect was not observed.

In contrast, in the case where both of the nitrate and citric acid were blended in addition to peracetic acid, not only was the weight loss percentage lowered, but additionally, almost no appearance change (occurrence of rust, tarnish) was observed, and an obvious corrosion-suppressing effect was observed. The corrosion-suppressing effect was improved as the amount of the nitrate and citric acid blended in the acidic-oxidant-containing solution was increased, and there was a correlation between them.

(1) Acidic-Oxidant-Containing Aqueous Solution

Experimental Example 2

Peracetic acid was used as the acidic oxidant. Specifically, as shown in Table 4, acidic-oxidant-containing aqueous solutions (pH 4 to 6) (Test Liquids 16 to 18) were prepared; in each of which, potassium nitrate (1 w/w %) and citric acid (1 w/w %) were blended in addition to peracetic acid (1 w/w %), using the above-described artificial hard water. The pH was adjusted using potassium hydroxide. For comparison, acidic-oxidant-containing aqueous solutions (pH 4 to 6) (Test Liquids 19 to 20) were prepared; in each of which, peracetic acid (1 w/w %), without potassium nitrate or citric acid, was blended using the artificial hard water and potassium hydroxide.

(2) Corrosiveness Test

Subject 1 (test piece A5052) (the same type as that used in Experimental Example 1) was immersed in the acidic-oxidant-containing aqueous solutions (Test Liquids 16 to 20) (room temperature: 20 to 25° C.) in a similar manner as in Experimental Example 1, and withdrawn after three days. Then, the degree of corrosion was studied from the appearance change and weight loss percentage (%) using the same criteria as that used in Experimental Example 1.

Table 4 shows the degree of corrosion (appearance change and weight loss percentage (%)) of subject 1 immersed in each test liquid.

TABLE 4

| Test liquid | Peracetic acid (w/w %) | Potassium nitrate (w/w %) | Citric acid (w/w %) | pH | Wight loss percentage (%) | Appearance change |
|---|---|---|---|---|---|---|
| 16 | 1 | 1 | 1 | 4 | 0.02 | ⊚ |
| 17 | 1 | 1 | 1 | 6 | −0.02 | ⊚ |
| 18 | 1 | 1 | 1 | 8 | −0.01 | ⊚ |
| 19 | 1 | 0 | 0 | 4 | −6.54 | X |
| 20 | 1 | 0 | 0 | 6 | −1.22 | X |

As seen from the table, it was observed that aluminium corrosion (weight loss, appearance change (occurrence of rust, tarnish)) due to peracetic acid having a high concentration (1 w/w %) was remarkably suppressed using the nitrate and the carboxylic acid (citric acid) in combination.

Experimental Example 3

(1) Acidic-Oxidant-Containing Aqueous Solution

Hydrogen peroxide was used as the acidic oxidant. Specifically, as shown in Table 5, acidic-oxidant-containing aqueous solutions (pH 5 to 6) (Test Liquids 21 to 22) were prepared; in each of which, potassium nitrate (2 w/w %) and citric acid (2 w/w %) were blended in addition to hydrogen peroxide (15 w/w %) using the above-described artificial hard water. The pH was adjusted using potassium hydroxide. For comparison, acidic-oxidant-containing aqueous solutions (pH 5 to 6) (Test Liquids 23 to 24) were prepared; in each of which, hydrogen peroxide (15 w/w %), without potassium nitrate or citric acid, was blended using the artificial hard water and potassium hydroxide.

(2) Corrosiveness Test

Subject 1 (test piece A5052) (the same type as that used in Experimental Example 1) was immersed in the acidic-oxidant-containing aqueous solutions (Test Liquids 21 to 24) (room temperature: 20 to 25° C.) in a similar manner as in Experimental Example 1, and withdrawn after three days. Then, the degree of corrosion was studied from the appearance change and weight loss percentage (%) using the same criteria as that used in Experimental Example 1.

Table 5 shows the degree of corrosion (appearance change and weight loss percentage (%)) of each subject.

TABLE 5

| Test liquid | Hydrogen peroxide (w/w %) | Potassium nitrate (w/w %) | Citric acid (w/w %) | pH | Weight loss percentage (%) | Appearance change |
|---|---|---|---|---|---|---|
| 21 | 15 | 2 | 2 | 5 | −0.04 | ⊚ |
| 22 | 15 | 2 | 2 | 6 | −0.04 | ⊚ |
| 23 | 15 | 0 | 0 | 5 | −0.05 | X |
| 24 | 15 | 0 | 0 | 6 | −0.03 | Δ |

As seen from the table, it was observed that aluminium corrosion (weight loss, appearance change (occurrence of rust, tarnish)) due to hydrogen peroxide having a high concentration (15 w/w %) was remarkably suppressed (Test Liquids 21 to 22) using the nitrate and the carboxylic acid (citric acid) in combination.

Experimental Example 4

(1) Acidic-Oxidant-Containing Aqueous Solution

Peracetic acid was used as the acidic oxidant. Specifically, acidic-oxidant-containing aqueous solutions were prepared in which peracetic acid (0.3 w/w %), potassium nitrate (10 w/w %), and the carboxylic acids listed in Table 6 (malic acid, succinic acid, lactic acid) were blended using the above-described artificial hard water; and the final pH was adjusted to pH 3.5 using a potassium hydroxide solution (Test Liquids 25 to 28; however Test Liquid 25 did not contain any carboxylic acid).

TABLE 6

| | Carboxylic acid | | |
|---|---|---|---|
| Test liquid | Type | Blending amount (w/w %) | pH of final acidic-oxidant-containing aqueous solution |
| 25 | — | 0 | 3.5 |
| 26 | malic acid | 10.5 | 3.5 |
| 27 | succinic acid | 2.7 | 3.5 |
| 28 | lactic acid | 14.1 | 3.5 |

(2) Corrosiveness Test

Subjects 1 to 3 (test pieces A5052, A5056, A6061) (the same types as those used in Experimental Example 1) were immersed in the acidic-oxidant-containing aqueous solutions (Test Liquids 25 to 28) (mom temperature: 20 to 22° C.) in a similar manner as in Experimental Example 1, and withdrawn after seven days (after 1 week). Then, the degree of corrosion was studied from the appearance change and weight loss percentage (%) using the same criteria as that used in Experimental Example 1.

Table 7 shows the degree of corrosion (appearance change and weight loss percentage (%)) of the subjects immersed in the test liquids.

TABLE 7

| | Subject 1 Test piece A5052 | | Subject 2 Test piece A5056 | | Subject 3 Test piece A6061 | |
|---|---|---|---|---|---|---|
| Test liquid | Weight loss percentage | Appearance change | Weight loss percentage | Appearance change | Weight loss percentage | Appearance change |
| 25 | 0.00% | Δ | 0.02% | X | 0.07% | X |
| 26 | −0.01% | ⊚ | −0.10% | ⊚ | −0.12% | ⊚ |
| 27 | 0.02% | ○ | 0.05% | ⊚ | 0.02% | ⊚ |
| 28 | −0.01% | ⊚ | 0.03% | ⊚ | −0.02% | ⊚ |

As seen from the table, corrosion-suppressing effects (reduction of weight loss percentage, suppression of appearance change (occurrence of rust, tarnish)) were also observed in the case where malic acid, succinic acid, or lactic acid was used as the carboxylic acid used in combination with the nitrate; as in the case where citric acid was used.

Experimental Example 5

(1) Acidic-Oxidant-Containing Aqueous Solution

Hydrogen peroxide was used as the acidic oxidant. Specifically, acidic-oxidant-containing aqueous solutions (Test Liquids 29 to 31) (pH 3.5) were prepared in which potassium nitrate and citric acid were blended at the proportions listed in Table 8 in addition to hydrogen peroxide 7.5 w/w % using the above-described artificial hard water. Test Liquid 31 was adjusted to have pH 3.5 using potassium hydroxide.

TABLE 8

| Test liquid | Hydrogen peroxide (w/w %) | Potassium nitrate (w/w %) | Citric acid (w/w %) | pH |
|---|---|---|---|---|
| 29 | 7.5 | 0 | 0.1 | 3.5 |
| 30 | 7.5 | 2 | 0.1 | 3.5 |
| 31 | 7.5 | 2 | 2 | 3.5 |

(2) Corrosiveness Test

Subjects 1 to 3 (test pieces A5052, A5056, A6061) were immersed in the acidic-oxidant-containing aqueous solutions (Test Liquids 29 to 31) (room temperature: 20 to 25° C.) in a similar manner as in Experimental Example 1, and withdrawn after seven days (after 1 week). Then, the degree of corrosion was studied from the appearance change and weight loss percentage (%) using the same criteria as that used in Experimental Example 1.

Table 9 shows the degree of corrosion (appearance change and weight loss percentage (%)) of the subjects immersed in the test liquids.

TABLE 9

| Test liquid | Subject 1 Test piece A5052 | | Subject 2 Test piece A5056 | | Subject 3 Test piece A6061 | |
|---|---|---|---|---|---|---|
| | Weight loss percentage | Appearance change | Weight loss percentage | Appearance change | Weight loss percentage | Appearance change |
| 29 | −0.04% | Δ | −0.06% | Δ | −0.03% | Δ |
| 30 | −0.01% | ○ | −0.03% | ◎ | 0.00% | ○ |
| 31 | −0.06% | ◎ | −0.07% | ◎ | −0.02% | ◎ |

As seen from the table, it was observed that in the case where the pH was adjusted to 3.5 using hydrogen peroxide as the acidic oxidant, although the weight loss of the aluminium alloys was small, an appearance change (occurrence of rust, tarnish) occurred (Test Liquid 29). In contrast, it was observed that such an appearance change (occurrence of rust, tarnish) was obviously suppressed using the nitrate and the carboxylic acid in combination with hydrogen peroxide (Test Liquids 30 and 31).

Experimental Example 6

(1) Acidic-Oxidant-Containing Aqueous Solution

Hydrogen peroxide was used as the acidic oxidant. Specifically, acidic-oxidant-containing aqueous solutions (Test liquids 32 to 33) were prepared; in each of which, potassium nitrate and citric acid were blended at the proportions listed in Table 10 in addition to hydrogen peroxide 3 w/w % using the above-described artificial hard water. Each test liquid was adjusted to have pH 2 using nitric acid.

TABLE 10

| Test liquid | Hydrogen peroxide (w/w %) | Potassium nitrate (w/w %) | Citric acid (w/w %) | pH |
|---|---|---|---|---|
| 32 | 3 | 0 | 1 | 2 |
| 33 | 3 | 1 | 1 | 2 |

(2) Corrosiveness Test

Subject 1 (test piece A5052) was immersed in the acidic-oxidant-containing aqueous solutions (Test Liquids 32 and 33) (room temperature: 20 to 25° C.) in a similar manner as in Experimental Example 1, and withdrawn after 24 hours. Then, the degree of corrosion was studied from the appearance change and weight loss percentage (%) using the same criteria as that used in Experimental Example 1. Table 11 shows the degree of corrosion (appearance change and weight loss percentage (%)) of the subject 1 immersed in each test liquid. It should be noted that the results shown below are average values obtained from two subject pieces (n=2).

TABLE 11

| Test liquid | Subject 1 Test Piece A5052 | |
|---|---|---|
| | Weight loss percentage | Appearance change |
| 32 | 0.09% | X |
| 33 | −0.05% | ◎ |

As seen from the table, it was observed that, in the case where hydrogen peroxide was used as the acidic oxidant, even when the hydrogen peroxide had a low concentration of 3 wt %, an appearance change (occurrence of rust, tarnish) occurred (Test Liquid 32). It was observed that such an appearance change (occurrence of rust, tarnish) was remarkably suppressed (Test Liquid 33) using the nitrate and the carboxylic acid (citric acid) in combination with hydrogen peroxide.

Experimental Example 7

(1) Acidic-Oxidant-Containing Aqueous Solution

Peracetic acid was used as the acidic oxidant. Specifically, acidic-oxidant-containing aqueous solutions (Test Liquids 34 to 37) containing nitric acid and citric acid at the proportions listed in Table 12 in addition to peracetic acid 0.3 w/w % were prepared using the above-described artificial hard water. Test Liquids 34 and 35 were adjusted to have pH 1 and Test Liquids 36 and 37 were adjusted to have pH 2 using potassium hydroxide.

TABLE 12

| Test liquid | Peracetic acid (w/w %) | Nitric acid (w/w %) | Citric acid (w/w %) | pH |
|---|---|---|---|---|
| 34 | 0.3 | 2 | 0 | 1 |
| 35 | 0.3 | 2 | 2 | 1 |
| 36 | 0.3 | 2 | 0 | 2 |
| 37 | 0.3 | 2 | 2 | 2 |

(2) Corrosiveness Test

Subjects 1 to 3 (test pieces A5052, A5056 and A6061) were immersed in the acidic-oxidant-containing aqueous solutions (Test Liquids 34 to 37) (room temperature: 20 to 25° C.) in a similar manner as in Experimental Example 1, and withdrawn after seven days (after 1 week). Then, the degree of corrosion was studied from the appearance change and weight loss percentage (%) using the same criteria as that used in Experimental Example 1.

Table 13 shows the degree of corrosion (appearance change (occurrence of rust, tarnish) and weight loss percentage (%)) of the subjects immersed in the test liquids.

TABLE 13

| Test liquid | Subject 1 Test piece A5052 | | Subject 2 Test piece A5056 | | Subject 3 Test piece A6061 | |
|---|---|---|---|---|---|---|
| | Weight loss percentage | Appearance change | Weight loss percentage | Appearance change | Weight loss percentage | Appearance change |
| 34 | −0.89% | ○ | −0.90% | ○ | −0.74% | ○ |
| 35 | −0.15% | ◎ | −0.33% | ◎ | −0.27% | ◎ |
| 36 | −0.17% | ◎ | −0.14% | ◎ | −0.08% | ◎ |
| 37 | −0.07% | ◎ | −0.07% | ◎ | −0.03% | ◎ |

As shown in the table, the weight loss of the aluminium alloys tended to increase as the acidity of the acidic-oxidant-containing aqueous solutions increased. However, it was observed that the weight loss and the appearance change (occurrence of rust, tarnish) of the aluminium alloys were suppressed by using nitric acid, or nitric acid in combination with the carboxylic acid.

Experimental Example 8

(1) Acidic-Oxidant-Containing Aqueous Solution

Peracetic acid was used as the acidic oxidant. Specifically, acidic-oxidant-containing aqueous solutions (Test Liquids 38 to 43) were prepared in which nitric acid and citric acid were blended at the proportions listed in Table 14 in addition to low-concentration peracetic acid 0.001 to 0.01 w/w % (10 ppm, 50 ppm, 100 ppm) using the above-described artificial hard water. Each test liquid was adjusted to have pH 2 using potassium hydroxide.

TABLE 14

| Test liquid | Peracetic acid (w/w %) | Nitric acid (w/w %) | Citric acid (w/w %) | pH |
|---|---|---|---|---|
| 38 | 0.001 | 0 | 0 | 2 |
| 39 | 0.001 | 0.1 | 0.1 | 2 |
| 40 | 0.005 | 0 | 0 | 2 |
| 41 | 0.005 | 0.1 | 0.1 | 2 |
| 42 | 0.01 | 0 | 0 | 2 |
| 43 | 0.01 | 0.1 | 0.1 | 2 |

(2) Corrosiveness Test

Subject 1 (test piece A5052) was immersed in the acidic-oxidant-containing aqueous solutions (Test Liquids 38 to 43) (room temperature: 20 to 25° C.) in a similar manner as in Experimental Example 1, and withdrawn after 24 hours. Then, the degree of corrosion was studied from the appearance change and weight loss percentage (%) using the same criteria as that used in Experimental Example 1.

Table 15 shows the degree of corrosion (appearance change (occurrence of rust, tarnish) and weight loss percentage (%)) of Subject 1 immersed in the test liquids.

TABLE 15

| Test liquid | Peracetic acid concentration (w/w %) | Subject 1 Test piece A5052 | |
|---|---|---|---|
| | | Weight loss percentage | Appearance change |
| 38 | 0.001 | −0.01% | ○ |
| 39 | 0.001 | 0.05% | ◎ |
| 40 | 0.005 | −0.09% | ○ |
| 41 | 0.005 | 0.03% | ◎ |
| 42 | 0.01 | −0.07% | Δ |
| 43 | 0.01 | −0.06% | ◎ |

As shown in the table, the weight loss of the aluminium alloy tended to increase as the concentration of the acidic oxidant in each acidic-oxidant-containing aqueous solution (Test Liquids 38 to 43) was increased. However, it was observed that the weight loss and the appearance change (occurrence of rust, tarnish) of the aluminium alloy were suppressed by using the carboxylic acid in combination with nitric acid.

As seen from the table, it was observed that, in the case where peracetic acid was used as the acidic oxidant, even when the peracetic acid had a low concentration of 10 ppm (0.001 wt %), a small appearance change (occurrence of rust, tarnish) occurred (Test Liquid 38). Moreover, the appearance change became more obvious as the concentration of the peracetic acid (Test Liquid 42) was increased. It was observed that such an appearance change (occurrence of rust, tarnish) was significantly suppressed (Test Liquids 39, 41 and 43) using the nitrate and the carboxylic acid in combination with peracetic acid.

Experimental Example 9

(1) Acidic-Oxidant-Containing Aqueous Solution

Peracetic acid was used as the acidic oxidant, and acidic-oxidant-containing aqueous solutions (pH 3.6) (Test Liquids 44 and 45) having the respective compositions shown in Table 16 were prepared using the artificial hard water.

TABLE 16

| Composition | Test liquid 44 | Test liquid 45 |
|---|---|---|
| Peracetic acid | 0.08 | 0.08 |
| Potassium nitrate | 0.1 | 0.1 |

TABLE 16-continued

| Composition | Test liquid 44 | Test liquid 45 |
|---|---|---|
| Citric acid | 0.2 | 0.01 |
| Citric acid sodium | — | 0.2 |
| Preservative (benzoic acid Na) | 0.0025 | 0.0025 |
| pH adjuster (potassium hydroxide) | 0.1 | — |
| Chelating agent (HEDP•4Na) | — | 0.02 |
| pH | 3.6 | 3.6 |

HEDP•4Na: tetrasodium of hydroxyethane diphosphonic acid (2) Corrosiveness Test

Subject 1 (test piece A5052) was immersed in the acidic-oxidant-containing aqueous solutions (Test Liquids 44 and 45) (temperature: 45° C.) in a similar manner as in Experimental Example 1, and withdrawn after 40 hours. Then, the degree of corrosion was studied from the appearance change and weight loss percentage (%) using the same criteria as that used in Experimental Example 1.

Table 17 shows the degree of corrosion (appearance change (occurrence of rust, tarnish) and weight loss percentage (%)) of subject 1 immersed in the test liquids.

TABLE 17

| Test liquid | Subject 1 Test piece A5052 | |
|---|---|---|
| | Weight loss percentage | Appearance change |
| 44 | −0.06 | ⊚ |
| 45 | −0.13 | ⊚ |

As shown in Table 17, it was observed that even in the case where the additives such as the preservative, and the chelating agent were blended into the acidic oxidant in addition to the nitrate and the carboxylic acid, the excellent aluminium corrosion-suppressing effect (weight loss suppression, appearance change (occurrence of rust, tarnish) suppression) due to the combined use of the nitrate and the carboxylic acid was nonetheless effectively maintained.

Experimental Example 10

(1) Acidic-Oxidant-Containing Aqueous Solution

Peracetic acid was used as the acidic oxidant, and an acidic-oxidant-containing aqueous solution (pH3.5) (Test Liquid 46) having the composition shown in Table 18 was prepared using the artificial hard water.

TABLE 18

| Composition | Test liquid 46 |
|---|---|
| Peracetic acid | 0.3 |
| Potassium nitrate | 0.4 |
| Citric acid | 0.1 |
| Buffer (trisodium phosphate) | 0.2 |
| Chelating agent (HEDP•4Na) | 0.03 |
| pH | 3.5 |

HPDP•4Na: tetrasodium of hydroxyethane diphosphonic acid (2) Corrosiveness Test

Subjects 1 to 3 (test piece A5052, A5056, A6061) were immersed in the acidic-oxidant-containing aqueous solution (Test Liquid 46) (room temperature: 20 to 25° C.) in a similar manner as in Experimental Example 1. The test liquid was replaced by a new one every week, and the weight loss percentage (%) was observed at each replacement. After four weeks, the subjects were withdrawn. The degree of corrosion was studied from the appearance change and weight loss percentage (%) using the same criteria as that used in Experimental Example 1.

Table 19 shows the degree of corrosion (appearance change (occurrence of rust, tarnish) and cumulative weight loss percentage (%)) of each subject.

TABLE 19

| Test liquid 46 | | Test piece A5052 | Test piece A5056 | Test piece A6061 |
|---|---|---|---|---|
| Cumulative weight change (%) | after 1 week | −0.04 | −0.22 | −0.12 |
| | after 2 weeks | −0.20 | −0.26 | −0.22 |
| | after 3 weeks | −0.27 | −0.40 | −0.33 |
| | after 4 weeks | −0.39 | −0.53 | −0.40 |
| Appearance change | after 4 weeks | ⊚ | ⊚ | ⊚ |

As shown in Table 19, it was observed that the excellent aluminium corrosion-suppressing effect (weight loss suppression, appearance change (occurrence of rust, tarnish) suppression) due to the combined use of the nitrate and the carboxylic acid was also nonetheless effectively maintained for a long period of time in the case where the chelating agent and the buffer were blended into the acidic oxidant in addition to the nitrate and the carboxylic acid.

FORMULATION EXAMPLES

Formulation Examples 1 to 2

One Part-Type Sterilization/Disinfection Liquid

Peracetic acid, hydrogen peroxide, potassium nitrate, citric acid, a chelating agent, and a buffer were blended and mixed at the proportions shown in the table below, respectively, to prepare a one part-type sterilization/disinfection liquid that can be used without being diluted.

TABLE 20

| | (wt. %) | |
|---|---|---|
| | Formulation Example 1 | Formulation Example 2 |
| Peracetic acid | 0.2% | 0.3% |
| Hydrogen peroxide | 0.3% | 0.4% |
| Potassium nitrate | 0.1% | 0.4% |
| Citric acid | 0.1% | 0.4% |
| Chelating agent (HEDP•4Na) | 0.01% | 0.1% |
| Buffer (trisodium phosphate) | 0.1% | 0.5% |

Formulation Example 3

Concentrated Two Part-Type Sterilization/Disinfection Liquid

Components were blended and mixed into water in accordance with the formulation below, and a first liquid and a second liquid were prepared, to prepare a concentrated two part-type sterilization/disinfection liquid. The sterilization/disinfection liquid can be used by mixing the first liquid, the second liquid and water at a ratio of 1:1:18 before use.

<First Liquid>

| | |
|---|---|
| peracetic acid | 6 wt % |
| hydrogen peroxide | 8 wt % |
| water | balance |
| total | 100 wt % |

<Second Liquid>

| | |
|---|---|
| potassium nitrate | 8 wt % |
| citric acid | 8 wt % |
| chelating agent (HEDP·4Na) | 10 wt % |
| buffer (trisodium phosphate) | 6 wt % |
| pH adjuster (potassium hydroxide) | 0.5 wt % |
| water | balance |
| total | 100 wt % |

Formulation Example 4

Concentrated Two Part-Type Sterilization/Disinfection Liquid

Components were blended and mixed into water in accordance with the formulation below; and a first liquid and a second liquid were prepared in order to prepare a concentrated two part-type sterilization/disinfection liquid. The sterilization/disinfection liquid can be used by mixing the first liquid, the second liquid, and water at a ratio of 1:3:296 before use.

<First Liquid>

| | |
|---|---|
| peracetic acid | 15 wt % |
| hydrogen peroxide | 22 wt % |
| water | balance |
| total | 100 wt % |

<Second Liquid>

| | |
|---|---|
| potassium nitrate | 10 wt % |
| citric acid | 10 wt % |
| chelating agent (HEDP·4Na) | 10 wt % |
| buffer (trisodium phosphate) | 5 wt % |
| pH adjuster (potassium hydroxide) | 5 wt % |
| water | balance |
| total | 100 wt % |

The invention claimed is:

1. A combination product comprising:
   (1) a first composition containing an acidic oxidant that is a combination of 5-15 wt % peracetic acid and 8-30 wt % hydrogen peroxide, wherein the first composition is in a first container, and
   (2) a second composition containing (a) an alkali metal salt of nitric acid, (b) at least one carboxylic acid selected from the group consisting of lactic acid, malic acid, succinic acid, and citric acid, or one or more salts thereof, and (c) at least one additive selected from the group consisting of chelating agents, stabilizing agents, preservatives, pH adjusters, and buffers, wherein the second composition is in a second container that is different from the first container.

2. The combination product according to claim 1, wherein the second composition contains 2-30 wt % of the alkali metal salt of nitric acid and 2-30 wt % of the carboxylic acid or salt thereof.

3. The combination product according to claim 2, wherein the second composition contains a chelating agent.

4. The combination product according to claim 1, wherein the second composition contains a chelating agent.

5. The combination product according to claim 1, wherein the first composition contains the acidic oxidant in an amount of 5-15 wt % peracetic acid and 8-22 wt % hydrogen peroxide.

6. The combination product according to claim 5, wherein the second composition contains 2-30 wt % of the alkali metal salt of nitric acid and 2-30 wt % of the carboxylic acid or salt thereof.

7. The combination product according to claim 5, wherein the second composition contains a chelating agent.

8. A method of using the combination product according to claim 1 comprising mixing the first composition and the second composition to provide a mixed composition and adjusting the pH of the mixed composition to be in the range of from 2 to 6.

9. The method of claim 8, wherein the first composition and the second composition are mixed to provide a mixed composition comprising (a) 0.05-1 wt % peracetic acid and 0.05-2 wt % hydrogen peroxide, (b) 0.1-10 wt % of the alkali metal salt of nitric acid, and (c) 0.1-30 wt % of the carboxylic acid or salt thereof.

10. The method of claim 8, wherein the second composition contains a chelating agent, and the mixed composition comprises 0.01-0.5 wt % of the chelating agent.

11. The method of claim 8, wherein the second composition contains 2-30 wt % of the alkali metal salt of nitric acid and 2-30 wt % of the carboxylic acid or salt thereof.

12. The method of claim 11, wherein the second composition contains a chelating agent, and the mixed composition comprises 0.01-0.5 wt % of the chelating agent.

13. The method of claim 11, wherein the first composition and the second composition are mixed to provide a mixed composition comprising (a) 0.05-1 wt % peracetic acid and 0.05-2 wt % hydrogen peroxide, (b) 0.1-10 wt % of the alkali metal salt of nitric acid, and (c) 0.1-30 wt % of the carboxylic acid or salt thereof.

14. The method of claim 8, wherein the first composition contains the acidic oxidant in an amount of 5-15 wt % peracetic acid and 8-22 wt % hydrogen peroxide.

15. The method of claim 14, wherein the second composition contains 2-30 wt % of the alkali metal salt of nitric acid and 2-30 wt % of the carboxylic acid or salt thereof.

16. The method of claim 14, wherein the second composition contains a chelating agent, and the mixed composition comprises 0.01-0.5 wt % of the chelating agent.

17. The method of claim 14, wherein the first composition and the second composition are mixed to provide a mixed composition comprising (a) 0.05-1 wt % peracetic acid and 0.05-2 wt % hydrogen peroxide, (b) 0.1-10 wt % of the alkali metal salt of nitric acid, and (c) 0.1-30 wt % of the carboxylic acid or salt thereof.

18. A disinfecting or sterilizing method comprising contacting (a) a surface containing, in part or in whole, aluminum or an aluminum alloy with (b) the combination product of claim 1.

19. The combination product according to claim 1, wherein the first composition is an aqueous solution consisting essentially of water and a combination of peracetic acid and hydrogen peroxide, as an acidic oxidant, wherein the peracetic acid exists as an equilibrium mixture of acetic acid and hydrogen peroxide.

\* \* \* \* \*